United States Patent
Hayashi et al.

(10) Patent No.: US 7,408,963 B2
(45) Date of Patent: Aug. 5, 2008

(54) MEDICAL LASER APPARATUS

(75) Inventors: Kenichi Hayashi, Gamagori (JP); Kazunobu Kojima, Gamagori (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 11/527,690

(22) Filed: Sep. 27, 2006

(65) Prior Publication Data
US 2007/0078449 A1   Apr. 5, 2007

(30) Foreign Application Priority Data
Sep. 30, 2005   (JP)   ............................... 2005-287947

(51) Int. Cl.
*H01S 3/30*   (2006.01)
*H01S 3/10*   (2006.01)
(52) U.S. Cl. .................. 372/21; 372/6; 372/22
(58) Field of Classification Search .............. 372/6, 372/21, 22, 39, 68, 96, 102
See application file for complete search history.

(56) References Cited

U.S. PATENT DOCUMENTS

| | | |
|---|---|---|
| 5,815,518 A | 9/1998 | Reed et al. |
| 6,061,369 A | 5/2000 | Conradi |
| 7,003,001 B2 * | 2/2006 | Sharma et al. ................. 372/3 |

FOREIGN PATENT DOCUMENTS

| | | |
|---|---|---|
| JP | A 11-054853 | 2/1999 |
| JP | A 2003-527741 | 9/2003 |
| JP | A 2004-321507 | 11/2004 |

\* cited by examiner

*Primary Examiner*—Armando Rodriguez
(74) *Attorney, Agent, or Firm*—Oliff & Berridge, PLC

(57) ABSTRACT

A medical laser apparatus suitable for medical treatment, which is capable of obtaining a plurality of visible laser beams each having a different wavelength, but which has an inexpensive structure.

A medical laser apparatus capable of selectively irradiating a plurality of visible laser beams each having a different wavelength onto an affected part, comprises: a fiber laser source unit including an excitation light source, a plurality of fiber lasers for oscillating, by means of excitation light from the excitation light source, a plurality of infrared fundamental beams each having a different wavelength and a first optical switch having an input portion and a plurality of output portions for selectively switching a transmission path of the excitation light from the excitation light source to one of the fiber lasers, the fiber laser source unit being capable of selectively oscillating the fundamental beams; and a plurality of wavelength conversion elements for wavelength-converting the fundamental beams, from the fiber laser source unit, to a plurality of visible second harmonic beams.

9 Claims, 4 Drawing Sheets

MEDICAL LASER APPARATUS

BACKGROUND OF THE INVENTION

1. Field of the Invention

The present invention relates to a medical laser apparatus capable of selectively irradiating a plurality of visible laser beams each having a different wavelength onto an affected part of a body.

2. Description of the Related Art

As a medical laser apparatus such as a laser apparatus for use in photo coagulation treatment in ophthalmology, a type including a Raman fiber laser and a wavelength conversion element, for obtaining a plurality of visible laser beams each having a different wavelength that is suitable for the treatment at high intensity, has been proposed.

However, in the case of using the Raman fiber laser, a considerable number of fiber Bragg gratings having appropriate characteristics corresponding to the wavelength of an infrared beam, which is the source of a visible beam that is being sought, need to be combined, thereby complicating the structure and resulting in a high level of costs. Moreover, in order to obtain a plurality of infrared beams each having a different wavelength, which are the sources of a plurality of visible beams each having a different wavelength, a plurality of expensive Raman fiber lasers corresponding to the respective wavelengths of the infrared beams needs to be used. Further, the Raman fiber laser entails a problem insofar that the width of a spectrum of a Raman shifted infrared beam is likely to expand so that wavelength-conversion efficiency of its wavelength conversion element is reduced. Thus, if the intention is to obtain a visible beam of a level of more than 1 W (watt) that is necessary for the treatment, an excitation light source having a high level of output becomes necessary, thereby resulting in an expensive apparatus.

SUMMARY OF THE INVENTION

An object of the present invention is to provide a medical laser apparatus suitable for medical treatment, which is capable of obtaining a plurality of visible laser beams each having a different wavelength, but which has an inexpensive structure.

To achieve the object described above, the present invention has a configuration of the kind described below.

According to one aspect of the present invention, a medical laser apparatus is provided that is capable of selectively irradiating a plurality of visible laser beams each having a different wavelength onto an affected part, comprising: a fiber laser source unit including an excitation light source, a plurality of fiber lasers for oscillating, by means of excitation light from the excitation light source, a plurality of infrared fundamental beams each having a different wavelength and a first optical switch having an input portion and a plurality of output portions for selectively switching a transmission path of the excitation light from the excitation light source to one of the fiber lasers, the fiber laser source unit being capable of selectively oscillating the fundamental beams; and a plurality of wavelength conversion elements for wavelength-converting the fundamental beams, from the fiber laser source unit, to a plurality of visible second harmonic beams.

According to another aspect of the present invention, a medical laser apparatus is provided further comprising a fiber amplifier for amplifying intensity of the fundamental beams from the fiber laser source unit.

According to still another aspect of the present invention, a medical laser apparatus is provided further comprising a second optical switch having a plurality of input portions and an output portion for synthesizing transmission paths of the fundamental beams from the fiber lasers, wherein the fiber amplifier is connected to the output portion of the second optical switch.

According to a further aspect of the present invention, a medical laser apparatus is provided wherein the wavelength conversion elements are switchingly disposed on an optical path of the selectively oscillated fundamental beam.

According to a still further aspect of the present invention, a medical laser apparatus is provided wherein the wavelength conversion elements are disposed on optical paths, between an optical branching system and an optical multiplexing system, of the fundamental beams, respectively.

According to a yet still further aspect of the present invention, a medical laser apparatus is provided wherein the wavelength conversion elements are connected to the fiber lasers, respectively.

DESCRIPTION OF THE PREFERRED EMBODIMENTS

Figure 1:
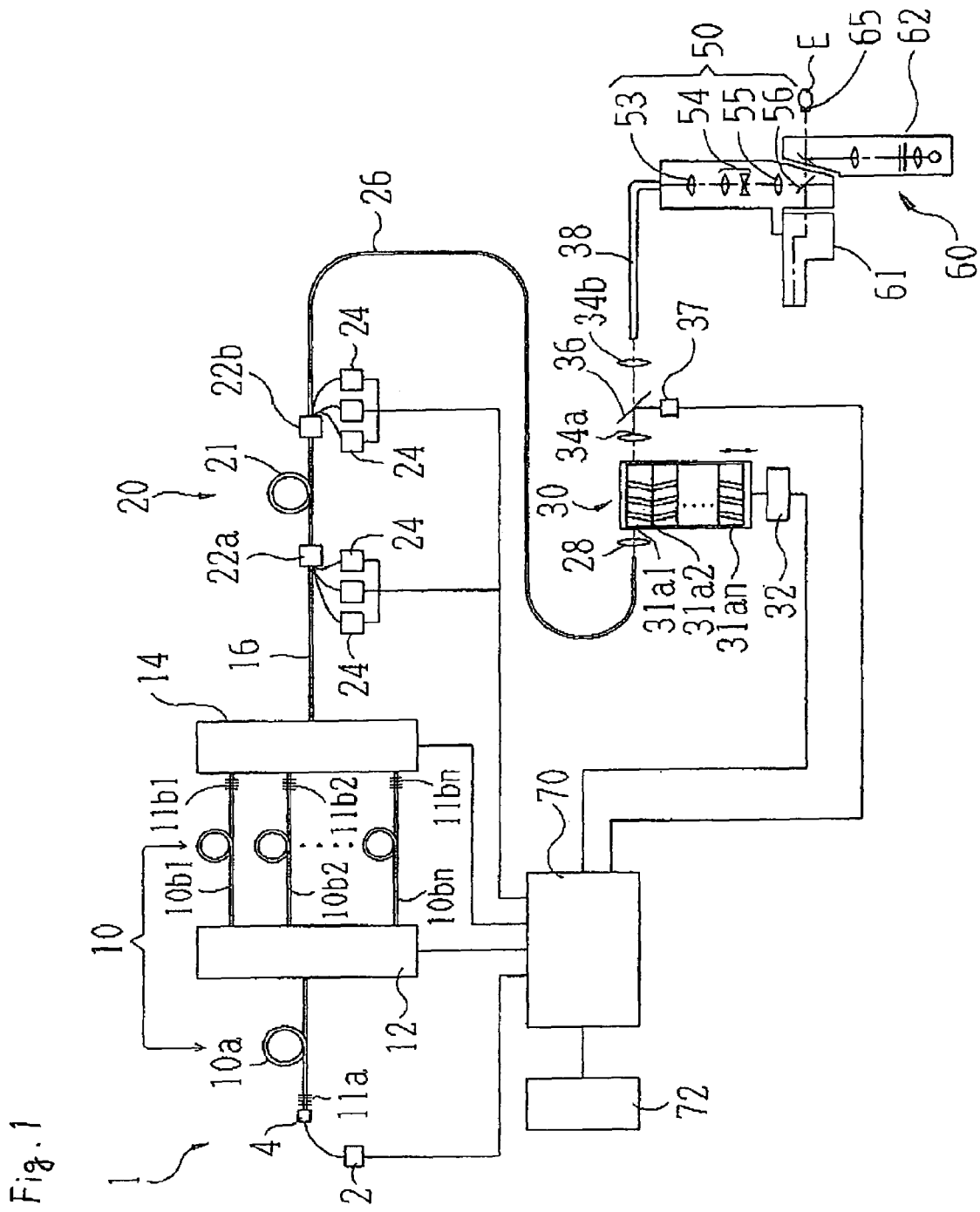
FIG. 1 is a schematic structure diagram of a laser apparatus for ophthalmology according to a first embodiment of the present invention.

Hereinafter, the preferred embodiments of the present invention will be described in detail with reference to the accompanying drawings. FIG. 1 is a schematic structure diagram of a laser apparatus for ophthalmology according to a first embodiment of the present invention.

Figure 2:
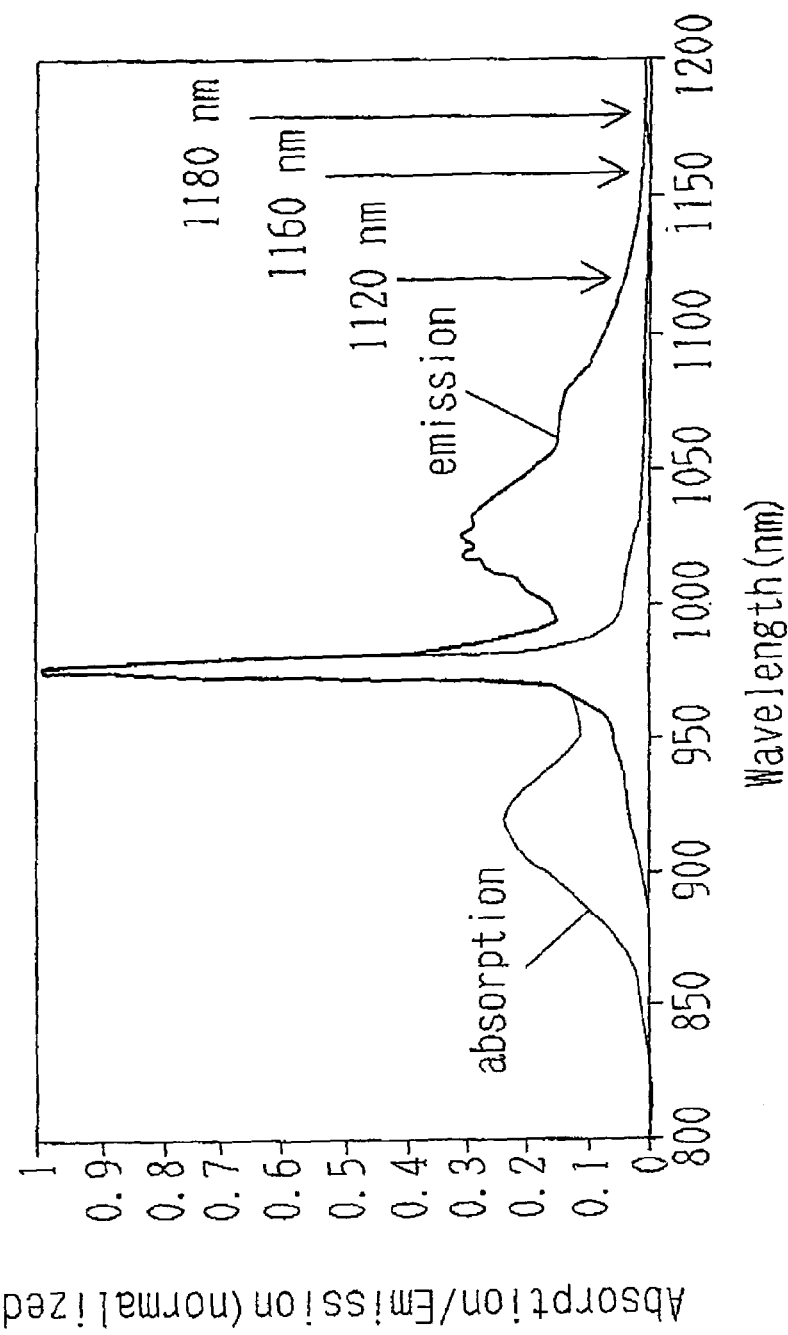
FIG. 2 is a diagram illustrating the absorption spectrum characteristics and the emission spectrum characteristics of a Yb glass fiber.

Excitation light having a wavelength of $\lambda p$ (for example, a wavelength of 980 nm) outputted from a laser diode (hereinafter referred to as a LD) 2, as an excitation light source, is inputted to a fiber laser 10 through a coupler 4. The fiber laser 10 comprises a first fiber laser 10a onto which the excitation light from the LD 2 is inputted and N number of second fiber lasers 10b1-10bn. The first fiber laser 10a and the second fiber lasers 10b1-10bn are made of a Yb glass fiber in which yttrium (hereinafter referred to as Yb) is doped into a core portion thereof. The Yb glass fiber can oscillate at least from an infrared beam having a wavelength of 1040 nm-1080 nm, which is a fundamental beam of a second, green, harmonic beam having a wavelength of 520 nm-540 nm, to an infrared beam having a wavelength of 1160 nm-1200 nm, which is a fundamental beam of a second, orange, harmonic beam having a wavelength of 580 nm-600 nm (see FIG. 2). A plurality of LDs 2 may be used.

An input end of the first fiber laser 10a is connected to the coupler 4, and an output end of the first fiber laser 10a is connected to an input portion of an optical switch 12, which is a transmission optical path switching (selection) unit. The optical switch 12 has an input portion and N number of output portions. Further, input ends of the second fiber lasers 10b1-10bn are connected to the output portions of the optical switch 12. A fiber Bragg grating (hereinafter referred to as a FBG)

11a is formed at the input end of the first fiber laser 10a. On the other hand, FBG 11b1-11bn are formed at output ends of the second fiber lasers 10b1-10bn. The FBG 11a has characteristics of enabling the excitation light having the wavelength of $\lambda p$ from the LD 2 to pass through, and of substantially reflecting fundamental beams having wavelengths of from $\lambda 1$ to $\lambda n$ that have been oscillated from the second fiber lasers 10b1-10bn. The FBGs 11b1-11bn have characteristics of substantially reflecting the excitation light having the wavelength of $\lambda p$, and of enabling a part of the fundamental beams having the wavelengths of from $\lambda 1$ to $\lambda n$ to pass through. In other words, a resonator for the fundamental beams having the wavelengths of from $\lambda 1$ to $\lambda n$ is specified by the FBG 11a of the first fiber laser 10a, and by the FBGs 11b1-11bn of the second fiber lasers 10b1-10bn. Further, by the first fiber laser 10a and any one of the second fiber lasers 10b1-10bn selected by the optical switch 12, a fundamental beam having a wavelength corresponding to the second fiber laser that has been selected is oscillated.

A fiber laser source unit 1 comprises the excitation light source 2; the coupler 4; the first fiber laser 10a, in which the FBG 11a is formed; the optical switch 12; and the second fiber lasers 10b1-10bn, in which the FBGs 11b1-11bn are formed.

As the structure of the fiber laser 10, it is permissible not to use the first fiber laser 10a. In other words, it is permissible to form the FBG 11a (11a1-11an) at the input ends of the second fiber lasers 10b1-10bn, and to input the excitation light from the LD 2 directly onto the optical switch 12, thereby ensuring that the fundamental beams having the wavelengths of from $\lambda 1$ to $\lambda n$ are oscillated by only the second fiber lasers 10b1-10bn. However, if the first fiber laser 10a is not used, the FBG 11a needs to be formed for each of the second fiber lasers 10b1-10bn and further, fibers of lengths that are sufficient for oscillating the fundamental beams having the wavelengths of from $\lambda 1$ to $\lambda n$ are necessary. In contrast to this, if the first fiber laser 10a is used, the quantity (number) of the FBGs 11a can be reduced by using the first fiber laser 10a that is common to the fundamental beams of the wavelengths of from $\lambda 1$ to $\lambda n$, and the lengths of the fibers which are used for the second fiber lasers 10b1-10bn can be reduced. To do so is advantageous in terms of costs, and, moreover, the amount of load that is applied to the optical switch 12 can be reduced.

The output ends of the second fiber lasers 10b1-10bn are connected to input portions of an optical switch 14, which is a transmission optical path synthesizing unit The optical switch 14 has N number of input portions and an output portion. An input end of a transmission fiber 16 is connected to the output portion of the optical switch 14. A fiber amplifier 20 is connected to an output end of the transmission fiber 16. The fiber amplifier 20 comprises an amplification fiber 21 composed of the same Yb glass fiber as the fiber laser 10, couplers 22a and 22b, disposed at both ends of the amplification fiber 21, and a plurality of LDs 24 connected to each of the couplers 22a and 22b. Excitation light in the same direction as the signal light from the transmission fiber 16, and excitation light in an opposite direction, are inputted onto the amplification fiber 21 so as to amplify the intensity of the fundamental beam(s) from the transmission fiber 16. Further, an isolator (not shown), for preventing the return of the excitation light, is disposed on the input side of the fiber amplifier 20, and a wavelength fiber (not shown), for enabling the amplified fundamental beam(s) to pass through, is disposed on the output side of the fiber amplifier 20.

According to this first embodiment, the fiber amplifier 20 for amplifying the fundamental beam(s) is provided on an optical path on which transmission paths of the fundamental beams from the second fiber lasers 10b1-10bn are synthesized by the optical switch 14. In consequence, the intensity of the fundamental beam(s) oscillated by the fiber laser source unit 1 can be reduced, thereby reducing the amount of load that is applied onto the optical switches 12 and 14. In contrast to the communication field, photocoagulation treatment in ophthalmology requires a visible treatment beam of more than 1 W. Assuming that wavelength-conversion efficiency of a wavelength conversion element is 20%, if the intention is to obtain a visible second harmonic beam of 1 W after the wavelength-conversion, a fundamental beam of 5 W is required. If the intention is to obtain a fundamental beam of more than 5 W by means of the fiber laser source unit 1, it is also necessary to use an optical switch that is capable of coping with high intensity. In contrast to this, because in the first embodiment the intensity of the fundamental beam oscillated by the fiber laser source unit 1 can be lowered to less than 1 W, an inexpensive optical switch may be used, which does not need to cope with high intensity. Additionally, the service life of the optical switch need not be reduced.

Although in the past the Raman fiber laser has encountered a problem insofar the width of a spectrum of an infrared fundamental beam that has been Raman-shifted has tended to expand, the width of the spectrum of the fundamental beam dose not need to expand because the embodiment ensures that the infrared fundamental beam that is converted in wavelength by the second, orange, harmonic beam can be obtained by the fiber laser and further, the wavelength-conversion efficiency of the wavelength conversion element, can be enhanced. Thus, in comparison with the Raman fiber laser, the intensity of the fundamental beam inputted onto the wavelength conversion element can be lowered, thereby reducing the quantity (number) of expensive LDs that need to be used.

An input end of a transmission fiber 26 is connected to the fiber amplifier 20. A focusing lens 28 and a wavelength conversion unit 30 are disposed on an optical path extending out from an output end of the transmission fiber 26. The wavelength conversion unit 30 contains a plurality of wavelength conversion elements 31a1-31an for converting the fundamental beams, from the fiber laser source unit 1, to the second harmonic beams. The wavelength conversion unit 30 is selectively moved by a drive unit 32 so that one of the wavelength conversion elements 31a1-31an is disposed on an optical axis of the focusing lens 28 (an optical path of the fundamental beam(s)).

The second harmonic beam(s) converted in wavelength by the wavelength conversion unit 30 is guided into a light guiding fiber 38 by focusing lenses 34a and 34b. A beam splitter 36 for separating a part of the second harmonic beam(s) is disposed between the focusing lens 34a and the focusing lens 34b, and an output sensor 37 is disposed on an optical path on an opposite side to the beam splitter 36.

The second harmonic beam(s) guided into the light guiding fiber 38 enters into a light-guiding optical system 50. In the meantime, the fundamental beam(s) that has not been converted in wavelength by the wavelength conversion unit 30 is absorbed by a damper optical system (not shown) that is disposed in a space extending up to the beam splitter 36.

The light-guiding optical system 50 includes a relay lens 53, zoom lenses 54 for changing the spot size of the beam, an objective lens 55, and a mirror 56 for reflecting the beam into a patient's eye E. The light-guiding optical system 50 is installed on a microscope portion 61 of a slit lamp 60 for observing the patient's eye E. The patient's eye E is illuminated by an illuminating portion 62 of the slit lamp 60. In the photo coagulation treatment, the visible second harmonic beam(s) guided by the light-guiding optical system 50 is irradiated onto a fundus of the patient's eye E, through a contact lens 65.

The LDs 2 and 24, the optical switches 12 and 14, the drive unit 32 and the output sensor 37 are connected to a control unit 70. An operation unit 72 for inputting factors such as conditions that need to be satisfied for the photo coagulation treatment is also connected to the control unit 70. The operation unit 72 includes items of equipment such as a wavelength-selecting switch for the treatment beam, an intensity-adjusting switch for the treatment beam and an irradiation time-setting switch for the treatment beam.

The operation of the apparatus having the structure described above will now be explained. The apparatus of this embodiment is made so as to select treatment beams of three wavelengths, of from $\lambda 1$ to $\lambda 3$. The treatment beam of the first wavelength $\lambda 1$ is produced as a result of converting, by means of the corresponding wavelength conversion element 31a1, an infrared fundamental beam having a center wavelength of 1060 nm oscillated by the second fiber laser 10b1 to a second, green, harmonic beam having a central wavelength of 530 nm. The treatment beam of the second wavelength $\lambda 2$ is produced as a result of converting, by means of the corresponding wavelength conversion element 31a2, an infrared fundamental beam having a central wavelength of 1120 nm oscillated by the second fiber laser 10b2 to a second, yellow, harmonic beam having a central wavelength of 560 nm. The treatment beam of the third wavelength $\lambda 3$ is produced as a result of converting, by means of the corresponding wavelength conversion element 31a3, an infrared fundamental beam having a central wavelength of 1160 nm oscillated by the second fiber laser 10b3 to a second, orange, harmonic beam having a central wavelength of 580 nm.

If the orange beam is selected by the wavelength-selecting switch as the treatment beam, in accordance with a wavelength-selecting signal, the control unit 70 connects an output of the optical switch 12 and an input of the optical switch 14 to the second fiber laser 10b3. As a result, the infrared fundamental beam having the central wavelength of 1160 nm is oscillated by the second fiber laser 10b3 and then, the infrared fundamental beam having the central wavelength of 1160 nm is outputted from the fiber laser source unit 1 through the optical switch 14.

The control unit 70 controls the drive unit 32 in accordance with the wavelength-selecting signal so as to dispose the wavelength conversion element 31a3 at a predetermined position on the optical axis of the focusing lens 28. In consequence, the infrared fundamental beam having the central wavelength of 1160 nm from the fiber laser source unit 1 is converted to the second harmonic beam having the central wavelength of 580 nm.

Because the intensity of the fundamental beam having the central wavelength of 1160 nm from the fiber laser source unit 1 is lower than that of the fundamental beams of other wavelengths, the control unit 70 adjusts the intensity of the excitation light from the LDs 24 to a relatively high value that has been set in advance. Further, the control unit 70 controls the output of the LDs 24 on the basis of a detection signal of the output sensor 37 so that the intensity of the second harmonic beam having the central wavelength of 580 nm can be stabilized at the intensity that has been set by the intensity-adjusting switch.

The second harmonic beam(s) that has been converted in wavelength is irradiated onto the patient's eye E through the light guiding fiber 38 and the light-guiding optical system 50.

When the green beam is selected by the wavelength-selecting switch as the treatment beam, the control unit 70 connects the output of the optical switch 12 and the input of the optical switch 14 to the second fiber laser 10b1. Further, the control unit 70 controls the drive unit 32 so as to dispose the wavelength conversion element 31a1 at the predetermined position on the optical axis of the focusing lens 28. In consequence, the infrared fundamental beam having the central wavelength of 1060 nm from the fiber laser source unit 1 is converted to the second, green, harmonic beam having the wavelength of 530 nm. Furthermore, because the intensity of the fundamental beam having the central wavelength of 1060 nm from the fiber laser source unit 1 is higher than that of the fundamental beams of other wavelengths, the control unit 70 adjusts the intensity of the excitation light from the LDs 24 to a relatively low value that has been set in advance. The control unit 70 controls the output of the LDs 24 on the basis of a detection signal of the output sensor 37 so that the intensity of the second harmonic beam having the central wavelength of 530 nm can be stabilized at the intensity that has been set by the intensity-adjusting switch.

When the yellow beam is selected by the wavelength-selecting switch as the treatment beam, the control unit 70 connects the output of the optical switch 12 and the input of the optical switch 14 to the second fiber laser 10b2. Further, the control unit 70 controls the drive unit 32 so as to dispose the wavelength conversion element 31a2 at the predetermined position on the optical axis of the focusing lens 28. In consequence, the infrared fundamental beam having the central wavelength of 1120 nm from the fiber laser source unit 1 is converted to the second, yellow, harmonic beam having the central wavelength of 560 nm. Furthermore, because the intensity of the fundamental beam having the central wavelength of 1120 nm from the fiber laser source unit 1 is higher than that of the fundamental beam having the central wavelength of 1160 nm, and is lower than that of the fundamental beam having the central wavelength of 1060 nm, the control unit 70 adjusts the intensity of the excitation light from the LDs 24 to an approximately intermediate value that has been set in advance. The control unit 70 controls the output of the LDs 24 on the basis of a detection signal of the output sensor 37 so that the intensity of the second harmonic beam having the central wavelength of 560 nm can be stabilized at the intensity that has been set by the intensity-adjusting switch.

Figure 3:
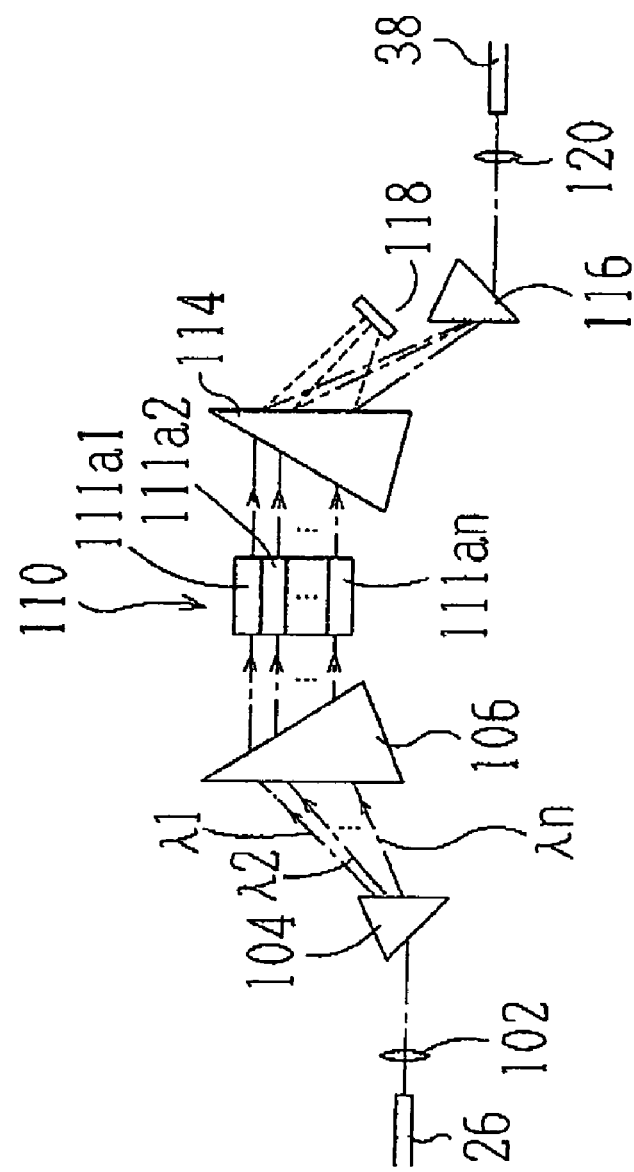
FIG. 3 is a schematic structure diagram illustrating another example of switching means for wavelength conversion elements.

Means for switching the wavelength conversion elements may be constructed as follows. FIG. 3 is a schematic structure drawing illustrating another example of the switching means of the wavelength conversion elements. The fundamental beam(s) from the transmission fiber 26 is transformed by the lens 102 into a parallel beam and then diffused spatially by a prism 104, which is an optical branching system, so as to correspond to each wavelength. In other words, the fundamental beams of wavelengths of from $\lambda 1$ to $\lambda n$ are deflected by the prism 104 in varying directions corresponding to each wavelength. A prism 106 deflects the fundamental beams so as to make parallel to one another optical paths of the fundamental beams that have been diffused. A wavelength conversion unit 110 is disposed on the optical paths of the fundamental beams deflected by the prism 106. The wavelength conversion unit 110 is constituted of a plurality of wavelength conversion elements 111a1-111an for converting the fundamental beams of the wavelengths of from $\lambda 1$ to $\lambda n$ to the second harmonic beams, and the wavelength conversion elements 111a1-111an are disposed on the optical paths of the fundamental beams of each corresponding wavelength, respectively. Optical paths of the second harmonic beams converted by the wavelength conversion elements 111a1-111an are synthesized into a single optical path by prisms 114 and 116, which constitute an optical multiplexing system.

Further, the fundamental beam(s) that has not been converted in wavelength by the wavelength conversion elements 111a1-111an are deflected by the prism 114 in directions that substantially vary from those of the second harmonic beam(s) that has been converted in wavelength, and the fundamental beam(s) is then absorbed by a damper 118. In the same manner as in the first embodiment, the second harmonic beam(s) enters into the light guiding fiber 38 by means of a focusing lens 120. Because the mechanism for switching the wavelength conversion elements by moving them becomes unnecessary, the structure of the apparatus can in these circumstances be simplified.

Figure 4:
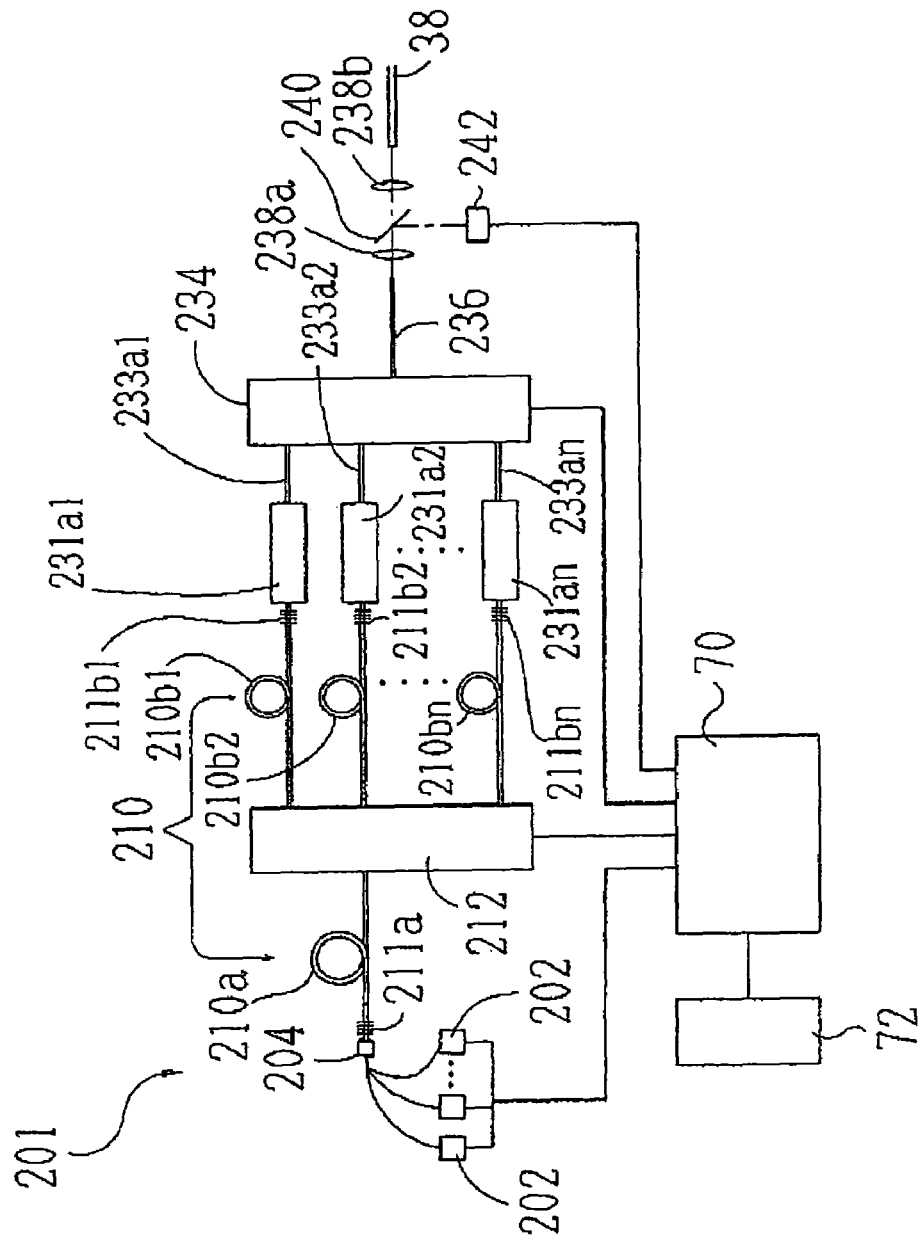
FIG. 4 is a schematic structure drawing of a laser apparatus for ophthalmology according to a second embodiment of the present invention.

FIG. 4 is a schematic structure drawing of a laser apparatus for ophthalmology according to a second embodiment of the present invention Identical reference numerals are annotated for the same components as in FIG. 1, and a description thereof is omitted.

A plurality of LDs 202 serving as an excitation light source are provided so as to be able to change the intensity of the excitation light to a considerable extent. The excitation light having a wavelength of $\lambda p$ (for example, a wavelength of 980 nm) outputted from the LDs 202 is inputted onto a fiber laser 210 through a coupler 204. The fiber laser 210 has the same structure as the fiber laser 10 and comprises a first fiber laser 210a onto which the excitation light from the LDs 202 is inputted, and N number of second fiber lasers 210b1-210bn. Like the optical switch 12, an optical switch 212 has an input portion and N number of output portions. Further, an output end of the first fiber laser 210a is connected to the input portion of the optical switch 212, and input ends of the second fiber lasers 210b1-210bn are connected to the output portions of the optical switch 212. FBG 211a of an identical type to the FBG 11a are formed at an input end of the first fiber laser 210a, and FBGs 211b1-211bn of an identical type to the FBGs 11b1-11bn are formed at output ends of the second fiber lasers 210b1-210bn. An fiber laser source unit 201 is constructed of the structure described above.

According to the second embodiment, and in contrast to the first embodiment, N number of wavelength conversion elements 231a1-231an for converting the fundamental beams to the second harmonic beams are connected to the output ends of N number of the second fiber lasers 210b1-210bn, respectively.

The wavelength conversion elements 231a1-231an are connected to input ends of transmission fibers 233a1-233an. Like the optical switch 14, an optical switch 234 has N number of input portions and an output portion. Output ends of the transmission fibers 233a1-233an are connected to the input portions of the optical switch 234, and an input end of a transmission fiber 236 is connected to the output portion of the optical switch 234. Focusing lenses 238a and 238b are disposed on an optical path extending out from an output end of the transmission fiber 236.

The second harmonic beam(s) emitted from the transmission fiber 236 after being converted in wavelength enters into the light-guiding fiber 38 by the focusing lenses 238a and 238b. A beam splitter 240 for separating a part of the second harmonic beam(s) is disposed between the focusing lens 238a and the focusing lens 238b, and an output sensor 242 is disposed on an optical path on an opposite side to the beam splitter 240.

The second harmonic beam(s) guided by the light guiding fiber 38 enters into the light-guiding optical system 50 and is irradiated onto the patient's eye E. Further, the fundamental beam(s) that has not been converted in wavelength is absorbed by a damper optical system (not shown) that is disposed in a space extending up to the beam splitter 240.

The LDs 202, the optical switches 212 and 234, the output sensor 242 and the operation unit 72 are connected to the control unit 70.

In the same manner as in the first embodiment, the apparatus of the second embodiment can select treatment beams of three wavelengths, of from $\lambda 1$ to $\lambda 3$. The treatment beam of the first wavelength $\lambda 1$ is produced as a result of converting, by means of the corresponding wavelength conversion element 231a1, an infrared fundamental beam having a center wavelength of 1060 nm oscillated by the second fiber laser 210b1 to a second, green, harmonic beam having a central wavelength of 530 nm. The treatment beam of the second wavelength $\lambda 2$ is produced as a result of converting, by means of the corresponding wavelength conversion element 231a2, an infrared fundamental beam having a central wavelength of 1120 nm oscillated by the second fiber laser 210b2 to a second, yellow, harmonic beam having a central wavelength of 560 nm. The treatment beam of the third wavelength $\lambda 3$ is produced as a result of converting, by means of the corresponding wavelength conversion element 231a3, an infrared fundamental beam having a central wavelength of 1160 nm oscillated by the second fiber laser 210b3 to a second, orange, harmonic beam having a central wavelength of 580 nm.

If the wavelength (color) of the treatment beam is selected by the wavelength-selecting switch, the control unit 70 controls to switch the output of the optical switch 212 and the input of the optical switch 234 in accordance with a wavelength selecting signal. For example, if the orange beam is selected, the output of the optical switch 212 and the input of the optical switch 234 are connected to the fiber laser 210b3. In consequence, the infrared fundamental beam having the central wavelength of 1160 nm is oscillated by the fiber laser 210b3 and converted, by the wavelength conversion element 231a3, to the second, orange, harmonic beam having the central wavelength of 580 nm. The control unit 70 controls the output of the LDs 202 in such a way that the intensity of the second harmonic beam detected by the output sensor 242 is modified so as to become the intensity that has been set by the intensity-adjusting switch.

The second harmonic beam(s) that has been converted in wavelength is irradiated onto the patient's eye E through the light guiding fiber 38 and the light-guiding optical system 50.

Because, in contrast to the apparatus of the first embodiment, the apparatus of the second embodiment does not require the fiber amplifier and a switching mechanism of the wavelength conversion elements, the structure of the apparatus is simplified.

What is claimed is:

1. A medical laser apparatus capable of selectively irradiating a plurality of visible laser beams each having a different wavelength onto an affected part, comprising:
   an excitation light source;
   a first fiber laser being made of an yttrium glass fiber and being connected to the excitation light source, an input end of the first fiber laser being formed with a fiber Bragg grating;
   an optical switch having an input portion being connected to the first fiber laser, and a plurality of output portions;
   a plurality of second fiber lasers being made of an yttrium glass fiber and being connected to the output portions of the optical switch, an output end of each of the second fiber lasers being formed with a fiber Bragg grating,
   wherein the first fiber laser and the second fiber lasers oscillate, by means of excitation light from the excitation light source, a plurality of infrared fundamental beams each having a different wavelength, the first fiber laser and one of the second fiber lasers oscillate an infrared fundamental beam having a wavelength of 1160 nm to 1200 nm; and a plurality of wavelength conversion elements for wavelength-converting the infrared fundamental beams, from the first and second fiber lasers to a plurality of visible second harmonic beams each having a different wavelength, wherein one of the wavelength conversion elements wavelength-converts the infrared fundamental beam having the wavelength of 1160 nm to 1200 nm to an orange second harmonic beam having a wavelength of 580 nm to 600 nm.

2. A medical laser apparatus capable of selectively irradiating a plurality of visible laser beams each having a different wavelength onto an affected part, comprising:

a fiber laser source unit including an excitation light source, a plurality of fiber lasers for oscillating by means of excitation light from the excitation light source, a plurality of infrared fundamental beams each having a different wavelength, and a first optical switch having an input portion and a plurality of output portions for selectively switching a transmission path of the excitation light from the excitation light source to one of the fiber lasers, the fiber laser source unit being capable of selectively oscillating the fundamental beams;

a plurality of wavelength conversion elements for wavelength-converting the fundamental beams, from the fiber laser source unit, to a plurality of visible second harmonic beams each having a different wavelength; and a fiber amplifier for amplifying intensity of the fundamental beams from the fiber laser source unit.

3. The medical laser apparatus according to claim 2 further comprising a second optical switch having a plurality of input portions and an output portion for synthesizing transmission paths of the fundamental beams from the fiber lasers, wherein the fiber amplifier is connected to the output portion of the second optical switch.

4. The medical laser apparatus according to claim 1, wherein the wavelength conversion elements are switchingly disposed on an optical path of the fundamental beams.

5. The medical laser apparatus according to claim 1, wherein the wavelength conversion elements are disposed on optical paths, between an optical branching system and an optical multiplexing system, of the fundamental beams, respectively.

6. The medical laser apparatus according to claim 1, wherein the wavelength conversion elements are connected to the second fiber lasers, respectively.

7. A medical laser apparatus capable of selectively irradiating a plurality of visible laser beams each having a different wavelength onto an affected part, comprising:

an excitation light source;

a plurality of fiber lasers being made of an yttrium glass fiber and being connected to the excitation light source, input and output ends of each of the fiber lasers being formed with fiber Bragg gratings, wherein the fiber lasers oscillate, by means of excitation light from the excitation light source, a plurality of infrared fundamental beams each having a different wavelength, one of the fiber lasers oscillates an infrared fundamental beam having a wavelength of 1160 nm to 1200 nm; and a plurality of wavelength conversion elements for wavelength-converting the infrared fundamental beams, from the fiber lasers, to a plurality of visible second harmonic beams each having a different wavelength, wherein one of the wavelength conversion elements wavelength-converts the infrared fundamental beam having the wavelength of 1160 nm to 1200 nm to an orange second harmonic beam having a wavelength of 580 nm to 600 nm.

8. The medical laser apparatus according to claim 7 further comprising an optical switch having an input portion being connected to the excitation light source, and a plurality of output portions, wherein the fiber lasers are connected to the output portions of the optical switch.

9. A medical laser apparatus capable of irradiating a visible laser beam onto an affected part, comprising:

an excitation light source;

a fiber laser being made of an yttrium glass fiber and being connected to the excitation light source, input and output ends of the fiber laser being formed with fiber Bragg gratings, wherein the fiber laser oscillates, by means of excitation light from the excitation light source, an infrared fundamental beam having a wavelength of 1160 nm to 1200 nm; and a wavelength conversion element for wavelength-converting the infrared fundamental beam having the wavelength of 1160 nm to 1200 nm, from the fiber laser, to an orange second harmonic beam having a wavelength of 580 nm to 600 nm.

\* \* \* \* \*